United States Patent
Raghavan et al.

(10) Patent No.: US 6,413,969 B1
(45) Date of Patent: Jul. 2, 2002

(54) GATIFLOXACIN PENTAHYDRATE

(75) Inventors: Krishnaswamy S. Raghavan, Cranbury; Sunanda A. Ranadive, East Brunswick; Jack Z. Gougoutas, Princeton; John D. DiMarco, East Brunswick; William L. Parker, Pennington; Martha Davidovich, East Brunswick, all of NJ (US); Ann Newman, Lafayette, IN (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/932,045

(22) Filed: Aug. 17, 2001

Related U.S. Application Data

(60) Provisional application No. 60/232,293, filed on Sep. 13, 2000.

(51) Int. Cl.[7] ............ A61K 31/496; C07D 401/10
(52) U.S. Cl. ............... 514/253.08; 544/363
(58) Field of Search .............. 544/363; 514/253.08

(56) References Cited

U.S. PATENT DOCUMENTS 5,043,450 A * 8/1991 Masuzawa et al. ......... 546/156
5,880,283 A * 3/1999 Matsumoto et al. ........ 544/363

* cited by examiner

*Primary Examiner*—Emily Bernhardt
(74) *Attorney, Agent, or Firm*—David M. Morse

(57) ABSTRACT

There are provided in accordance with the present invention crystalline gatifloxacin pentahydrate represented by the formula

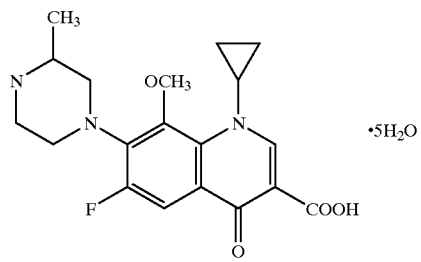

in a highly homogeneous form with respect to other crystalline forms thereof.

8 Claims, 5 Drawing Sheets

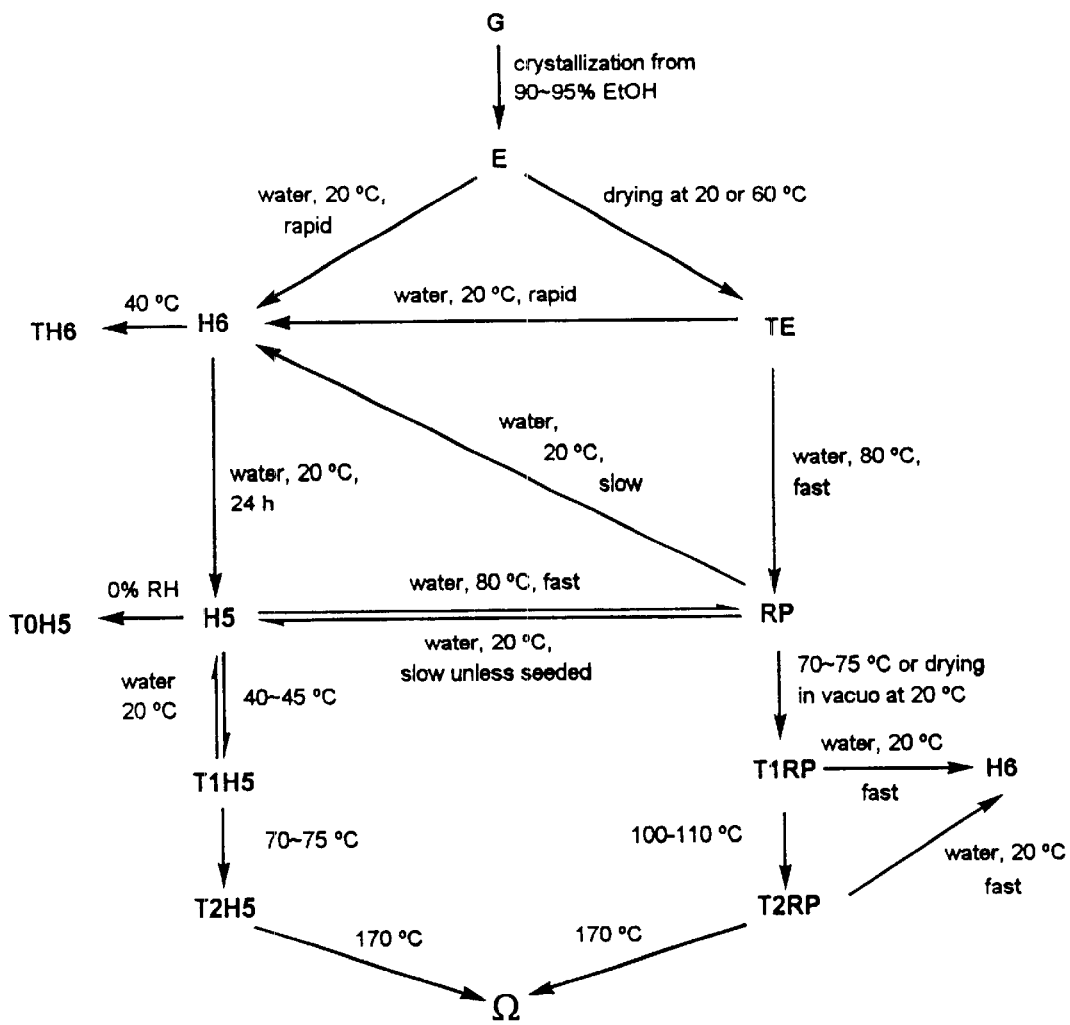

| | |
|---|---|
| G | Gatifloxacin |
| E | Ethanolate, six-sided platelets, gigantic solvent channels, very unstable in absence of mother liquor |
| TE | Transformed (desolvated) E, approximate hemihydrate, probably contains some T2RP |
| RP | Rectangular plates, sesqui-dihydrate |
| T1RP | Transformed RP |
| T2RP | Transformed T1RP, hemihydrate (monohydrate half occupied) |
| H5 | Pentahydrate, needles or rods or "wheat sheaves" |
| T0H5 | Transformed H5 at 0% RH |
| T1H5 | Transformed H5, monohydrate |
| T2H5 | Transformed T1H5 |
| H6 | Hexahydrate, rods |
| TH6 | Transformed H6 |
| Ω | High-temperature form |

(Single crystal X-ray structures have been determined for the underlined forms)

FIG. 1

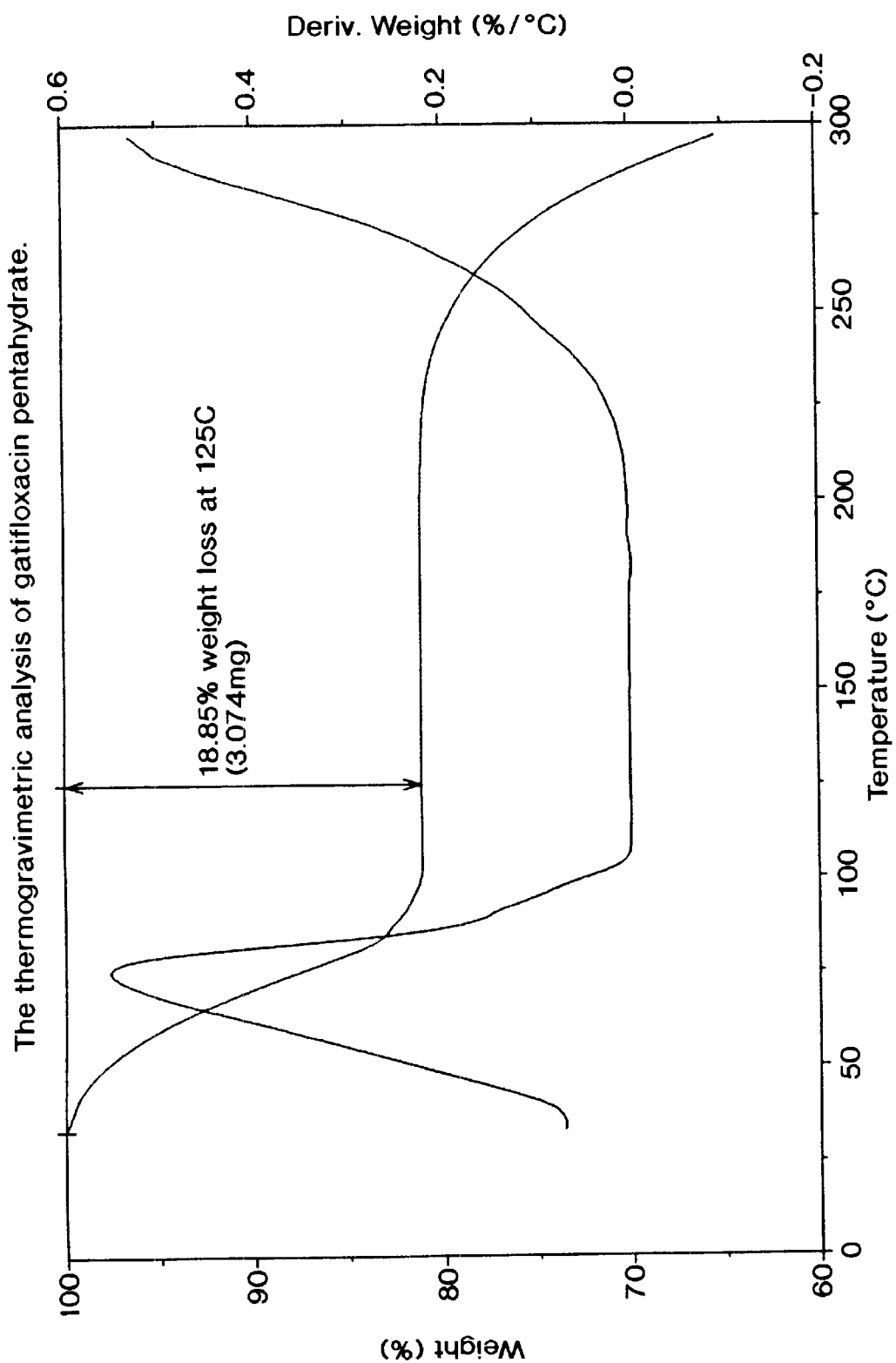

GATIFLOXACIN PENTAHYDRATE

CROSS REFERENCE TO RELATED APPLICATION

This application claims the benefit of U.S. Provisional Application Ser. No. 60/232,293 filed on Sep. 13, 2000.

FIELD OF THE INVENTION

The present invention relates to crystalline gatifloxacin pentahydrate and a process for producing it.

BACKGROUND OF THE INVENTION

Gatifloxacin, chemically 1-cyclopropyl-6-fluoro-1,4-dihydro-8-methoxy-7-(3-methyl-1piperizinyl)-4-oxo-3-quinolinecarboxylic acid, is represented by the following structure:

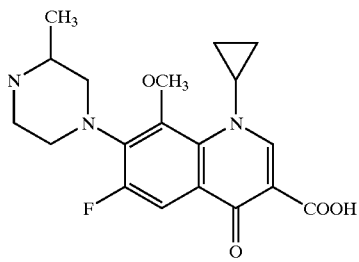

Gatifloxacin is a broad-spectrum quinolone antibiotic which is disclosed and claimed in U.S. Pat. No. 5,043,450 as being isolated as the hemihydrate. U.S. Pat. No. 5,880,283 discloses a sesquihydrate crystalline form of gatifoxacin that is disclosed as having advantages over the hemihydrate in pharmaceutical manufacturing. Such advantageous properties for the sesquihydrate in comparison to the hemihydrate include enhanced stability under varying conditions of humidity and superior disintegration and dissolution rates of tablets made therefrom.

Both the hemihydrate and the sesquihydrate forms have demonstrated a definite tendency to form higher hydrates in the presence of water.

In accordance with the present invention, it has been found that gatifloxacin pentahydrate in highly homogeneous form is advantageous to previously known forms and can be utilized to prepare stable pharmaceutical dosage forms, including an aqueous suspension, because it is the most physically stable form and does not have a tendency over time to convert to another crystalline form.

BRIEF DESCRIPTION OF THE DRAWINGS

FIG. 1 is an illustration of the interrelationship among the crystalline forms of gatifloxacin.

FIG. 5 is a thermogravimetric analysis of gatifloxacin pentahydrate.

SUMMARY OF THE INVENTION

Figure 2:
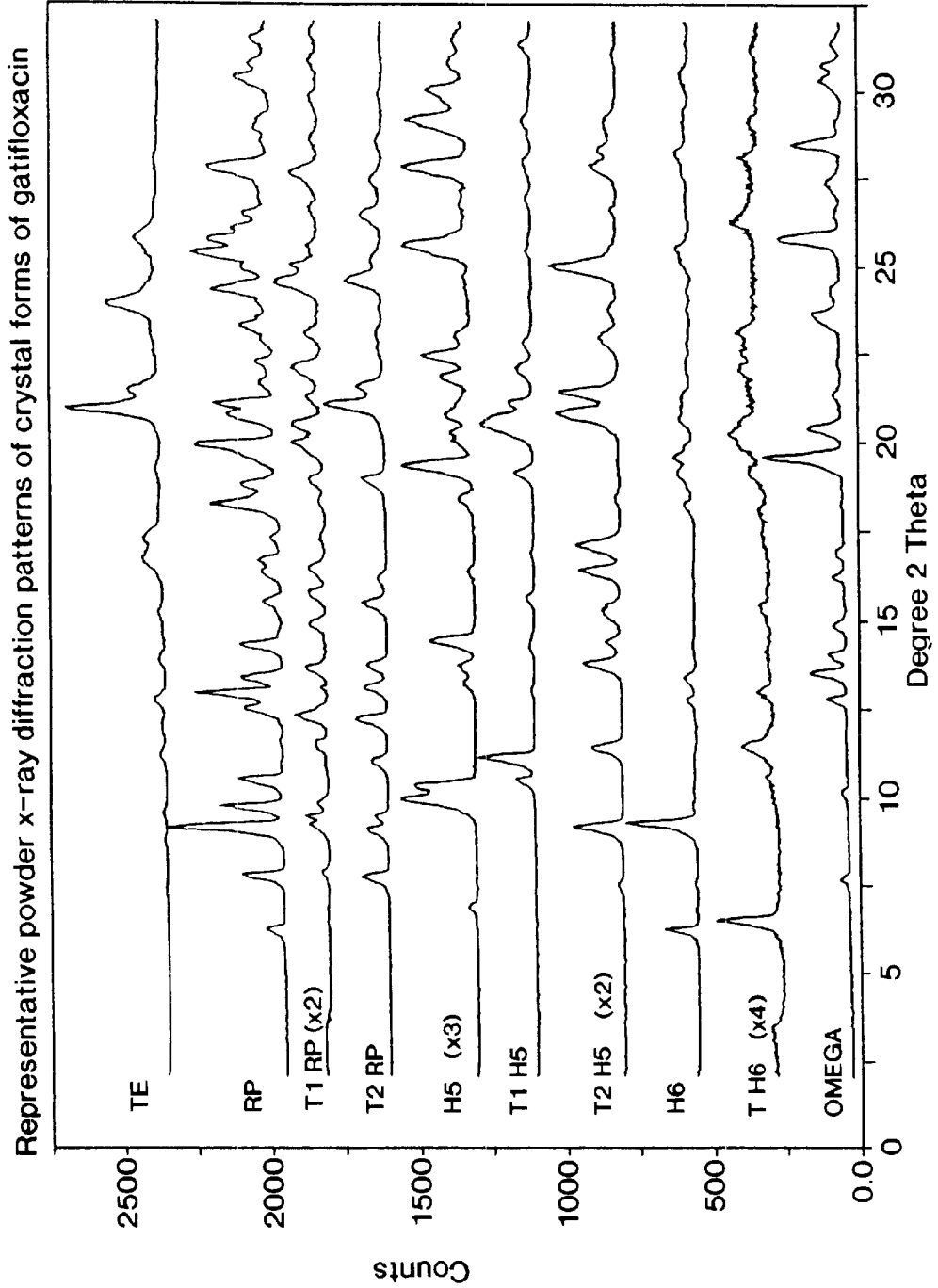
FIG. 2 shows the powder x-ray diffraction patterns of the pentahydrate and other crystalline forms of gatifloxacin.

In accordance with the present invention, there is provided a crystalline gatifloxacin pentahydrate which is highly homogeneous in regard to other crystalline forms thereof and has superior properties in comparison to such other crystalline forms. The present invention further pertains to a process for the preparation of homogeneous gatifloxacin pentahydrate, pharmaceutical formulations containing it and the use thereof in the treatment of a wide variety of infections.

DETAILED DESCRIPTION OF THE INVENTION

In accordance with the present invention, there is provided a novel highly homogenous crystalline pentahydrate form of the broad spectrum antibiotic gatifloxacin, 1cyclopropyl-6-fluoro-1,4-dihydro-8-methoxy-7-(3-methyl-1-piperazinyl)-4-oxo-3-quinolinecarboxylic acid, represented by the following structure:

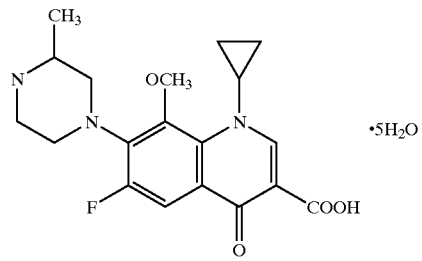

Gatifloxacin is approved for use as a broad spectrum antibacterial therapeutic agent. Gatifloxacin has been shown to be both safe and efficacious in the treatment of infections in individuals with impaired liver function. It has also been shown to be effective against a broad spectrum of microorganisms including antibiotic-resistant strains of *Streptococcus Pneumoniae* and to possess excellent overall tolerability.

The initial formulation process for the preparation of tablet dosage forms containing gatifloxacin sesquihydrate was a conventional wet granulation procedure. However, when a clinical batch of such tablets failed to conform to specifications, it was discovered by Differential Scanning Calorimetry that the pattern of the bulk material used in this batch was qualitatively different from that of the earlier small scale batches, and that this difference correlated with the failure of the tablets to meet performance specifications. Further investigation revealed a complex array of transformations involving a number of hydrated and anhydrous forms of the drug, principal among which were the sesquihydrate, the pentahydrate and the hexahydrate. In all, at least twelve different crystalline forms of gatifloxacin were identified and their interrelationships mapped as illustrated in FIG. 1.

The crystal structures and ideal water content of seven of these forms were established through single crystal x-ray analyses. Each form gives rise to unique and characteristic single crystal and powder x-ray diffraction. The kinetic and thermodynamic relationships among the three major hydrates were investigated leading to the understanding of their stability order in water as a function of temperature and their interconversion relationship. Further, the aqueous solubility relationship among them was found to parallel their thermodynamic stability order with the pentahydrate and sesquihydrate having the lowest and highest solubility at 25° C. respectively. The implications of these findings were very significant in the discovery and development of highly homogeneous gatifloxacin pentahydrate in accordance with the present invention. Further, these findings made it evident that very strict process controls were necessary in the production of crystalline gatifloxacin and dosage forms containing it and that it was necessary to obtain crystalline gatifloxacin pentahydrate in high homogeneity vs. the other crystalline forms in order to realize the advantageous properties thereof. By high homogeneity is meant that crystalline gatifloxacin pentahydrate must contain no detectable levels of the other crystalline forms thereof as determined by powder x-ray diffraction technique.

Gatifloxacin pentahydrate is further characterized by crystal parameters obtained from single crystal x-ray crystallographic analysis as set forth below.

Single Crystal Parameters of Gatifloxacin Pentahydrate:
Cell dimensions

| a = 9.339(1) angstrom | alpha = 106.55(2) degrees |
| b = 13.556(3) angstrom | beta = 91.93(1) degrees |
| c = 9.269(1) angstrom | gamma = 100.44(1) degrees |
| V = 1101.7(7) cubic angstrom | |

V=1101.7(7) cubic angstrom
Space group: P1 bar Triclinic
Molecules/unit cell=2
Density (calculated) (g/cubic cm)=1.403

Crystalline gatifloxacin pentahydrate may be prepared in high homogeneity by transforming the crude sesquihydrate product as formed by the process taught in U.S. Pat. No. 5,880,283. Gatifloxacin is initially crystallized from 90% ethanol as a highly solvated ethanolate (E in FIG. 1). The ethanolate desolvated to a crystalline product which approximates a hemihydrate (TE in FIG. 1). This product is rapidly transformed in water to the sesquihydrate (RP in FIG. 1) by heating to about 80° C. and slowly transformed to the hexahydrate (H6 in FIG. 1) at room temperature over a longer period. Continued equilibration of the hexahydrate product in water at room temperature will produce the pentahydrate (H5 in FIG. 1). Alternatively, once the pentahydrate has been formed and isolated, it may be utilized as seed crystals for a more rapid process of forming it from the sesquihydrate (or any other form). In this process, a small quantity of the pentahydrate, i.e. from about 0.1% to 2% by weight based on the weight of the sesquihydrate, is combined with the sesquihydrate (or any other crystalline form) and suspended in water with stirring at ambient temperature until conversion to the pentahydrate is completed, usually 24 hours or longer.

In addition to the crystalline forms of gatifloxacin described in the previous paragraph, other forms exist as illustrated in FIG. 1, which is a chart of the various forms and their process interrelations and FIG. 2, which shows the powder x-ray diffraction patterns of the various forms. In FIG. 1, the forms for which single crystal x-ray structures have been determined are indicated. Further, various equilibrium and kinetic transformations among the crystalline forms are indicated. The designations beginning with "T" indicate crystal forms produced by solid-solid transformations. Of the various crystalline forms of gatifloxacin, the primary ones that crystallize directly from aqueous solvents, as opposed to forms that crystallize from a molten phase or by solid-solid transformations, are the sesquihydrate, the hexahydrate and the pentahydrate.

Formation of the thermodynamically most stable form is a reasonable expectation for a solution mediated process, and using the most stable form rather than a metastable form is advantageous regarding physical stability of the crystalline form. The increased physical stability will afford additional advantages in formulation.

It has been found in accordance with the present invention that the advantageous stability and solubility properties of the pentahydrate of gatifloxacin can be applied to the formulation of pharmaceutical dosage forms. While the pentahydrate of gatifloxacin can be utilized to prepare tablets by wet granulation, it can also be formulated in accordance with the present invention into stable pharmaceutical solid dosage forms by conventional dry granulation. Stability studies on the pentahydrate form have demonstrated no evidence of form change or other degradation under stressed conditions of temperature and humidity, indicating that tablets made by dry granulation using the pentahydrate form are expected to be stable. Such formulations will include conventional inert ingredients such as binders, excipients, disintegrants, and the like. Examples of such agents include various starch derivatives such as pregelatinized starch, hydroxypropyl cellulose microcrystalline cellulose, sodium starch glycolate, magnesium stearate, lactose, mannitol and the like.

The pentahydrate of gatifloxacin is also more appropriate for the preparation of aqueous dosage forms than the metastable sesquihydrate in spite of being less soluble. This is commercially significant since gatifloxacin has demonstrated excellent efficacy both parenterally and via oral administration. Such oral formulations are formulated as ready to use suspensions or packaged as a dry powder suitable to be suspended in an appropriate amount of water just prior to use. The powder could be prepared by any conventional technique recognized in the art, but would preferably be formulated by mixing the highly homogeneous crystalline gatifloxacin pentahydrate with the other ingredients in powder form and the mixture packaged in an appropriate container. The other ingredients utilized to formulate such preparations would include conventional inert ingredients such as microcrystalline cellulose, methyl cellulose and the like, suitable sweetening and/or flavoring agents, and preservatives therefor if required. Such solid oral dosage forms or dry formulations suitable for the preparation of suspensions would be formulated such that they would contain an effective dose of gatifloxacin. In general, solid dosage forms containing 200 mg or 400 mg of gatifloxacin are contemplated. Preparations suitable for oral suspension would contain a similar dosage.

It is understood that various other embodiments and modifications in the practice of the invention will be apparent to, and can be readily made by, those of ordinary skill in the art without departing form the scope and spirit of the invention as described above. Accordingly, it is not intended that the scope of the claims appended hereto be limited to the exact description set forth above, but rather that the claims be construed as encompassing all of the features of patentable novelty that reside in the present invention, including all the features and embodiments that would be treated as equivalents thereof by those skilled in the relevant art. The invention is further described with reference to the following experimental work.

EXAMPLE 1

Preparation of Gatifloxacin Pentahydrate

The pentahydrate crystalline form is formed spontaneously from any other crystal form of gatifloxacin in equilibration in water at room temperature. A 1-g sample of gatifloxacin hemihydrate, prepared as described in U.S. Pat. No. 5,880,283, is suspended in 5 mL of water and stirred 24 hours at room temperature. The suspension is filtered with gentle suction and partially dried under suction for 2 hours. The resultant cake is further dried in a current of air at ambient pressure, temperature and humidity for 16 hours. The final product was analyzed by powder x-ray diffraction (FIG. 3), differential scanning calorimety (FIG. 4), thermogravimetric analysis (FIG. 5), and KF titration to confirm that it was the pentahydrate crystalline form of gatifloxacin.

Figure 3:
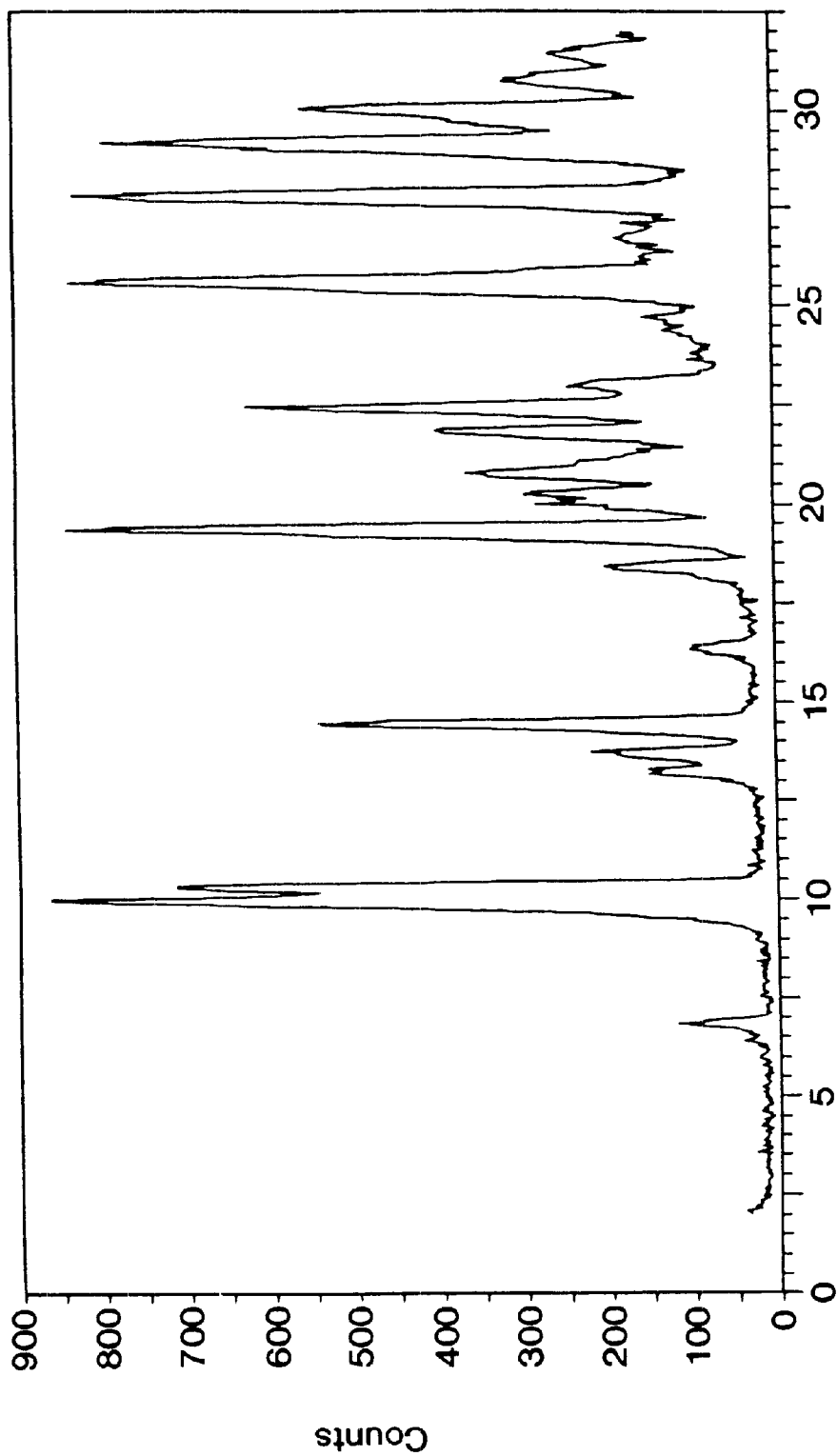
FIG. 3 is a powder x-ray diffraction pattern of gatifloxacin pentahydrate.

FIG. 3 shows the powder x-ray diffraction pattern of gatifloxacin pentahydrate.

Figure 4:
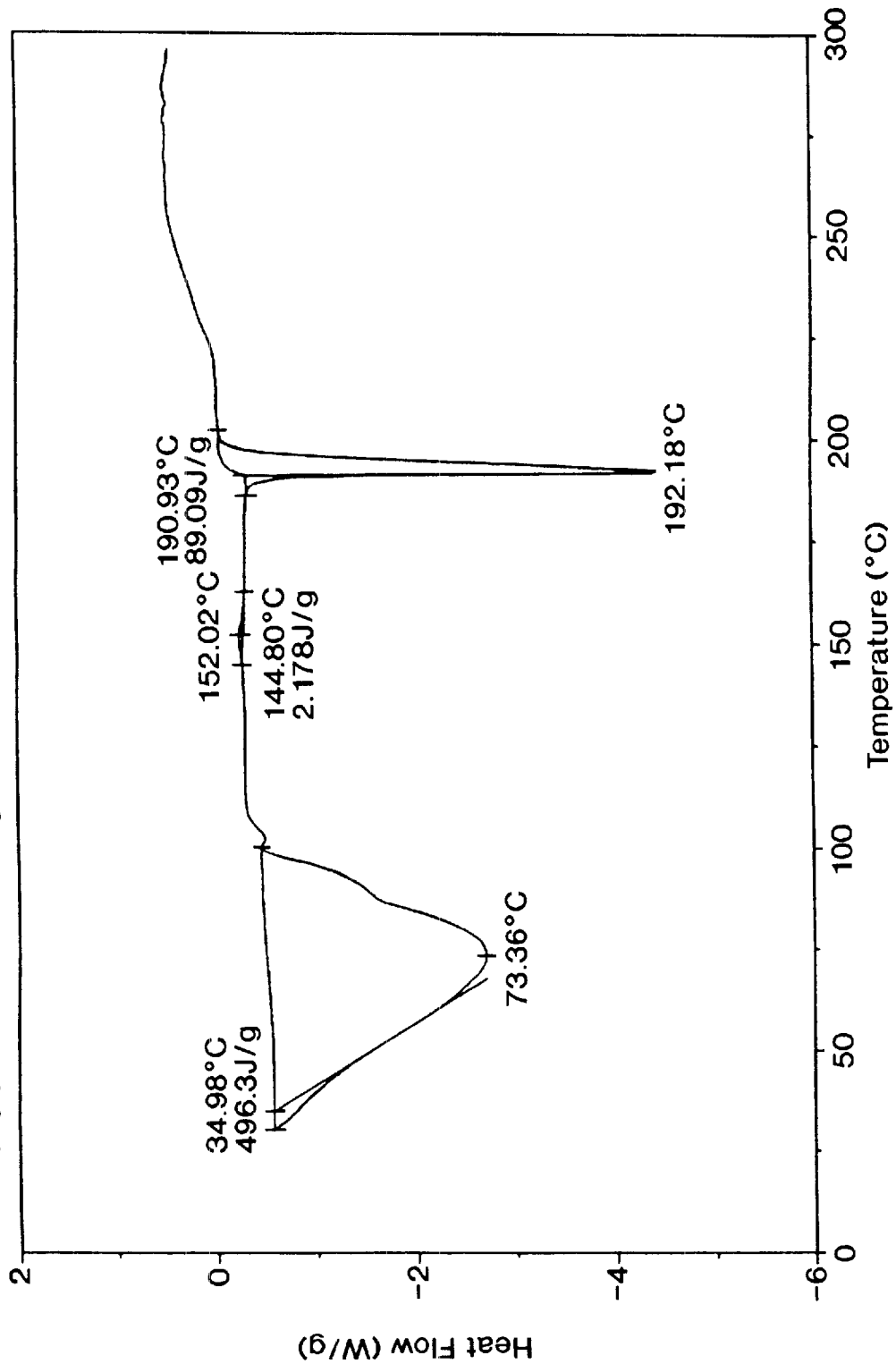
FIG. 4 is a differential scanning calorimetry analysis of gatifloxacin pentahydrate.

FIG. 4 shows the differential scanning calorimetry analysis of gatifloxacin pentahydrate.

FIG. 5 shows the thermogravimetric analysis of gatifloxacin pentahydrate.

EXAMPLE 2
Large Scale Production of Gatifloxacin Pentahydrate A 9.5-mg sample of gatifloxacin pentahydrate prepared as in Example 1 was ground with 0.01 mL of water in a mortar and pestle and transferred in 0.1 mL of waterto a flask containing 1.10 g of gatifloxacin sesquihydrate. Gatifloxacin sesquihydrate was prepared as described in U.S. Pat. No. 5,880,283. One mL of water was added and the mixture stirred for one hour at room temperature. Microscopic examination revealed partial conversion of the rectangular platelets characteristic of the sesquihydrate to the needles characteristic of the pentahydrate. This seed mixture, which had become too thick to flow, was diluted with 1 mL of water and added to a suspension of 599 g of gatifloxacin sesquihydrate in 600 mL of water. An additional 1800 mL of water was added, and the mixture was stirred gently at room temperature for 64 hours. Microscopic examination showed only needles, typically 1×40 to 3×75 micrometers. The mixture, which had the consistency of heavy cream, was filtered with gentle suction and partially dried in the funnel with the suction continually running for 23 hours. The resultant cake, which had the consistency of cream cheese, was sliced and dried at room temperature in a current of air at RH 50–60% for 28 hours. The solid (679 g) was passed through a 20 mesh screen to yield 666 g of powder. Further drying under ambient conditions produced no further weight loss. The final product had a water content of 19.4% by KF titration as expected for the pentahydrate (calculated 19.3%). The powder x-ray diffraction pattern confirmed that the product was gatifloxacin pentahydrate. Thermogravimetric analysis and differential scanning calorimetry also confirmed the pentahydrate form of the product.

EXAMPLE 3
Typical Composition of Gatifloxacin Pentahydate 100 mg Powder For Suspenion Gatifloxacin pentahydrate for oral suspension was prepared by combining the following ingredients in the amounts specified:

| Ingredient | Amount per 5 gram preparation |
| --- | --- |
| Gatifloxacin Pentahydrate | 107 mg* |
| Microcrystalline cellulose and sodium carboxymethylcellulose Avicel ® RC-591 | 50.0 mg |
| Methyl cellulose and sodium carboxymethylcellulose Methocel A4M Premium ® | 12.5 mg |
| Sucrose | 1000 mg |
| Flavoring agent, preservative | As needed |

*Equivalent to 100 mg of gatifloxacin/5 g suspension.

Avicel™ RC-591 is available from FMC Corporation
Methocel A4M Premium™ is available from Dow Chemical Co.

The ingredients were added in the order given and gently mixed. The resulting mixture was sealed in a suitable container. In use, the contents are combined with 3.8 g of water and shaken well to effect the suspension.

EXAMPLE 4
Typical Composition of Gatifloxacin Pentahydrate 400 mg Tablets

| Composition | Grams Per Tablet |
| --- | --- |
| Gatifloxacin pentahydrate | 0.428* |
| Microcrystalline cellulose | 0.138 |
| Sodium starch glycolate | 0.024 |
| Magnesium stearate | 0.009 |
| Total Tablet Weight | 0.600 |

*Equivalent to 400 mg of gatifloxacin

We claim:

1. Crystalline gatifloxacin pentahydrate represented by the formula

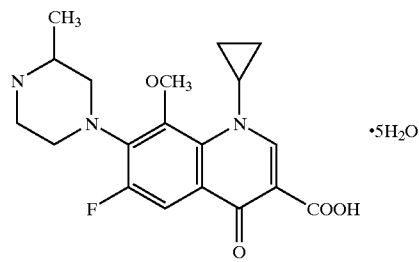

and characterized by single crystal parameters approximately equal to the following:

Cell dimensions

| | |
| --- | --- |
| a = 9.339(1) angstrom | alpha = 106.55(2) degrees |
| b = 13.556(3) angstrom | beta = 91.93(1) degrees |
| c = 9.269(l) angstrom | gamma = 100.44(1) degrees |
| V = 1101.7(7) cubic angstrom | |

Space group: P1 bar
Triclinic

Molecules/unit cell=2

Density (calculated) (g/cubic cm)=1.403, said crystalline gatifloxacin pentahydrate containing no detectable amounts of other gatifloxacin crystalline forms as determined by the powder x-ray diffraction technique.

2. A pharmaceutical composition which comprises as an active ingredient an amount of crystalline gatifloxacin pentahydrate as claimed in claim 1 and one or more pharmaceutically acceptable carriers, excipients or diluents.

3. A pharmaceutical composition in accordance with claim 2, wherein said composition is a solid dosage form for oral administration.

4. A pharmaceutical composition in accordance with claim 2, wherein said composition is a powder intended for suspension in water for oral administration.

5. A pharmaceutical composition in accordance with claim 2, wherein said composition is a ready to use suspension in water for oral administration.

6. A method for treating bacterial infections which comprises administering to a mammal in need thereof an effective amount of gatifloxacin pentahydrate as claimed in claim 1.

7. A method in accordance with claim 6 wherein crystalline gatifloxacin pentahydrate is administered parenterally.

8. A method in accordance with claim 6 wherein the crystalline gatifloxacin pentahydrate is administered orally.

* * * * *